United States Patent
Ammermann et al.

Patent Number: 5,891,908
Date of Patent: Apr. 6, 1999

[54] FUNGICIDAL MIXTURES

[75] Inventors: Eberhard Ammermann, Heppenheim; Gisela Lorenz, Hambach; Dietrich Mappes, Westheim; Klaus Schelberger, Gönnheim; Manfred Hampel, Neustadt, all of Germany

[73] Assignee: BASF Aktiengesellschaft, Ludwigshafen, Germany

[21] Appl. No.: 750,773

[22] PCT Filed: May 27, 1995

[86] PCT No.: PCT/EP95/02027

§ 371 Date: Dec. 10, 1996

§ 102(e) Date: Dec. 10, 1996

[87] PCT Pub. No.: WO95/34206

PCT Pub. Date: Dec. 21, 1995

[30] Foreign Application Priority Data

Jun. 10, 1994 [DE] Germany .......... 44 20 279.2

[51] Int. Cl.⁶ .......... A01N 37/12; A01N 37/34; A01N 37/44; A01N 47/10
[52] U.S. Cl. .......... 514/491; 514/476; 514/528; 514/539
[58] Field of Search .......... 514/528, 539, 514/476, 491

[56] References Cited

U.S. PATENT DOCUMENTS 4,829,085  5/1989  Wenderoth et al. .......... 514/522

FOREIGN PATENT DOCUMENTS

| 2131854 | 3/1995 | Canada . |
| 2132047 | 3/1995 | Canada . |
| 254 426 | 1/1988 | European Pat. Off. . |
| 645 089 | 3/1995 | European Pat. Off. . |
| 645 090 | 3/1995 | European Pat. Off. . |
| 2 267 644 | 12/1993 | United Kingdom . |
| 2 279 568 | 1/1995 | United Kingdom . |
| 95/15083 | 6/1995 | WIPO . |

OTHER PUBLICATIONS

Research Disclosure Nr. 338, 1992 Havant GB.
C. R. Worthing et al., The Pesticide Manual, 1991, The British Crop Protection Council, Farnham GB pp. 206–207.
Chem. Abstr., vol. 118, No. 23, Jun. 7, 1993 Abs. No. 228112.
WO, A, 95 15083 (Sumitomo Chem. Co., 8 Jun. 1995.

*Primary Examiner*—Allen J. Robinson
*Attorney, Agent, or Firm*—Keil & Weinkauf

[57] ABSTRACT

Fungicidal mixtures comprising
  a) the oxime ether carboxylic ester of the formula I

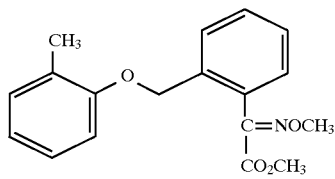

Ia

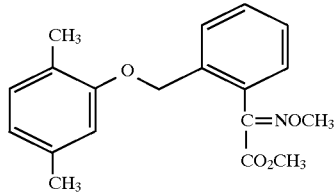

Ib and
  b) 1-(2-cyano-2-methoxyiminoacetyl)-3-ethylurea (II)

$$H_3CCH_2-NHCONH-C(CN)=NOCH_3 \quad \text{II}$$

in a synergistically effective amount.

8 Claims, No Drawings

FUNGICIDAL MIXTURES

This application is a 371 of PCT/EP95/02027 filed May 27, 1995.

The present invention relates to a fungicidal mixture which comprises a) an oxime ether carboxylic ester of the formula Ia or Ib

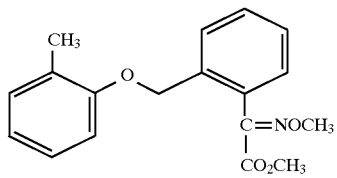

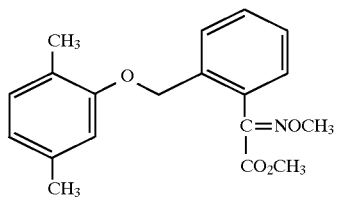

and b) 1-(2-cyano-2-methoxyiminoacetyl)-3-ethylurea (II)

in a synergistically effective amount.

The present invention also relates to a fungicidal mixture which, in addition to the oxime ether carboxylic ester of the formula I (or Ia or Ib) and the 1-(2-cyano-2-methoxyiminoacetyl)-3-ethyl-urea (II), comprises a dithiocarbamate III selected from the group manganese ethylenebis(dithiocarbamate) (zinc complex) (IIIa), manganese ethylenebis(dithiocarbamate) (IIIb), zinc ammoniate ethylenebis(dithiocarbamate) (IIIc) and zinc ethylenebis(dithiocarbamate) (IIId)

in a synergistically effective amount.

The invention additionally relates to methods for controlling harmful fungi using mixtures of the compounds I and II or mixtures of the compounds I, II and III and to the use of the compound I, the compound II and the compounds III for producing such mixtures.

The compounds of the formula Ia and Ib, their preparation and their action against harmful fungi are disclosed in the literature (EP-A 253 213).

The compound II (U.S. Pat. No. 3,957,847; common name: cymoxanil), its preparation and its action against harmful fungi are likewise known.

The dithiocarbamates III are likewise known (IIIa: common name: mancozeb, U.S. Pat. No. 3,379,610; IIIb: common name: maneb, U.S. Pat. No. 2,504,404; IIIc: former common name: metiram, U.S. Pat. No. 3,248,400; IIId: common name: zineb, U.S. Pat. No. 2,457,674).

It is an object of the present invention, with a view to reducing the application rates and improving the spectrum of action of the known compounds, to provide mixtures which have an improved effect on harmful fungi while the total amount of active ingredients applied is reduced (synergistic mixtures).

We have found that this object is achieved by the mixtures defined at the outset. We have also found that harmful fungi can be controlled better on simultaneous conjoint or separate use of the compounds I and II or I, II and III or on use of the compounds I and compound II and, if desired, of the compounds III successively than with the individual compounds.

The compounds of the formulae I and II can have the E or Z configuration for the C=N double bond (relative to the carboxyl group). Accordingly, they can each be used either as pure E or Z isomers or as E/Z isomer mixture in the mixture according to the invention. The E/Z isomer mixture or the E isomer is preferably used, and the E isomer is particularly preferred for the compound I.

Compound II is, because of the basic nature of the NH group, able to form salts or adducts with inorganic or organic acids or with metal ions.

Examples of inorganic acids are hydrohalic acids such as hydrofluoric acid, hydrochloric acid, hydrobromic acid and hydroiodic acid, sulfuric acid, phosphoric acid and nitric acid.

Formic acid, carbonic acid and alkanoic acids such as acetic acid, trifluoroacetic acid, trichloroacetic acid and propionic acid, and glycolic acid, thiocyanic acid, lactic acid, succinic acid, citric acid, benzoic acid, cinnamic acid, oxalic acid, alkylsulfonic acids (sulfonic acids with straight-chain or branched alkyl radicals with 1 to 20 carbon atoms), arylsulfonic acids or -disulfonic acids (aromatic radicals such as phenyl and naphthyl which carry one or two sulfo groups), alkylphosphonic acids (phosphonic acids with straight-chain or branched alkyl radicals with 1 to 20 carbon atoms), arylphosphonic acids or -diphosphonic acids (aromatic radicals such as phenyl and naphthyl which carry one or two phosphoric acid radicals), it being possible for the alkyl and aryl radicals to carry further substituents, eg. p-toluenesulfonic acid, salicylic acid, p-aminosalicylic acid, 2-phenoxybenzoic acid or 2-acetoxybenzoic acid etc for example as organic acids.

Particularly suitable metal ions are the ions of elements of the second main group, in particular calcium and magnesium, of the third and fourth main groups, in particular aluminum, tin and lead, and of the first to eighth transition groups, in particular chromium, manganese, iron, cobalt, nickel, copper, zinc and others. The metal ions of the elements of the transition groups of the fourth period are particularly preferred. The metals can moreover be present in the various valencies applying to them.

The pure active ingredients I and II are preferably employed in the preparation of the mixtures, which can as required be admixed with further active ingredients against harmful fungi or other pests such as insects, arachnids or nematodes, or else herbicidal or growth-regulating active ingredients or fertilizers.

The mixtures of compounds I and II and simultaneous conjoint or separate use of the compounds I and II are distinguished by an excellent action against a wide range of phytopathogenic fungi, in particular from the class of Ascomycetes and Basidiomycetes. Some of them have systemic activity and can therefore also be used as foliar and soil fungicides.

They are particularly important for controlling a large number of fungi on a variety of crop plants such as cotton, vegetables (eg. cucumbers, beans and cucurbits), barley, grass, oats, coffee, corn, fruit plants, rice, rye, soybean, grapevines, wheat, ornamental plants, sugar cane and a large number of seeds.

They are particularly suitable for controlling the following phytopathogenic fungi: Erysiphe graminis (powdery mildew) on cereals, Erysiphe cichoracearum and Sphaerotheca fuliginea on cucurbits, Podosphaera leucotricha on apples, Puccinia species on cereals, Rhizoctonia species on cotton and lawns, Ustilago species on cereals and sugar cane, Venturia inaequalis (scab) on apples, Helminthosporium species on cereals, Septoria nodorum on wheat, Botrytis cinera (gray mold) on strawberries and vines, Cercospora arachidicola on peanuts, Pseudocercosporella herpotrichoides on wheat and barley, Pyricularia oryzae on rice, Phytophthora infestans on potatoes and tomatoes, Plasmopara viticola on vines, Alternaria species on vegetables and fruit and Fusarium and Verticillium species.

They can also be used in material protection (eg. wood protection), for example against Paecilomyces variotii.

The compounds I and II or I, II and III can be applied simultaneously, together or separately, or successively, and the sequence of separate application generally has no effect on the result of control.

The compounds I and II are normally used in a ratio by weight of from 10:1 to 0.1:1, preferably 5:1 to 0.2:1, in particular 5:1 to 1:1.

The compounds I and III are normally used in a ratio by weight of from 1:50 to 1:2, preferably 1:40 to 1:1.8, in particular 1:30 to 1:1.5.

The application rates of the mixtures according to the invention depend on the nature of the desired effect and are from 0.01 to 3 kg/ha, preferably 0.1 to 1.5 kg/ha, in particular 0.1 to 1.0 kg/ha. The application rates are in these cases for compounds I from 0.01 to 0.5 kg/ha, preferably 0.05 to 0.5 kg/ha, in particular 0.05 to 0.4 kg/ha. The application rates for compounds II are correspondingly 0.01 to 0.5 kg/ha, preferably 0.05 to 0.5 kg/ha, in particular 0.05 to 0.4 kg/ha.

The application rate for the compounds III is generally from 0.1 to 10 kg/ha, preferably 0.5 to 5 kg/ha, in particular from 1 to 4 kg/ha.

The application rates of the mixture for seed treatment are generally from 0.001 to 50 g/kg of seeds, preferably 0.01 to 10 g/kg, in particular 0.01 to 8 g/kg.

Where harmful fungi which are pathogenic for plants are to be controlled, the separate or conjoint application of the compounds I and II or of the mixtures of compounds I, II and, if desired, III takes place by spraying or dusting the seeds, the plants or the soil before or after sowing the plants or before or after emergence of the plants.

The fungicidal synergistic mixtures according to the invention, or the compounds I, II and, if desired, III can be prepared, for example, in the form of directly sprayable solutions, powders and suspensions or in the form of high-percentage aqueous, oily or other suspensions, dispersions, emulsions, oily dispersions, pastes, dusting agents, scattering agents or granules, and be used by spraying, atomizing, dusting, scattering or pouring. The application form depends on the purpose of use; it should in every case ensure that dispersion of the mixture according to the invention is as fine and uniform as possible.

The formulations are produced in a conventional way, eg. by adding solvents and/or carriers. Inert additives such as emulsifiers or dispersants are normally mixed with the formulations.

Suitable surface-active substances are the alkali metal, alkaline earth metal, ammonium salts of aromatic sulfonic acids, eg. lignin-, phenol-, naphthalene- and dibutylnaphthalenesulfonic acid, and of fatty acids, alkyl- and alkylarylsulfonates, alkyl, lauryl ether and fatty alcohol sulfates, and salts of sulfated hexa-, hepta- and octadecanols or fatty alcohol glycol ethers, condensation products of sulfonated naphthalene and its derivatives with formaldehyde, condensation products of naphthalene or of naphthalenesulfonic acids with phenol and formaldehyde, polyoxyethylene octylphenol ethers, ethoxylated isooctyl-, octyl- or nonylphenol, alkylphenol or tributylphenyl polyglycol ether, alkylaryl polyether alcohols, isotridecyl alcohol, fatty alcohol ethylene oxide condensates, ethoxylated castor oil, polyoxyethylene alkyl ethers or polyoxypropylene, lauryl alcohol polyglycol ether acetate, sorbitol esters, lignin sulfite waste liquors or methylcellulose.

Scattering and dusting powders can be produced by mixing or milling together the compounds I, II and, if desired, III or the mixture of compounds I, II and, if desired, III with a solid carrier.

Granules (eg. coated, impregnated or homogeneous granules) are normally produced by binding the active ingredient or ingredients on to a solid carrier.

Examples of fillers and solid carriers which are used are mineral earths such as silica gel, silicas, silicates, talc, kaolin, limestone, lime, chalk, bole, loess, clay, dolomite, diatomaceous earth, calcium sulfate and magnesium sulfate, magnesium oxide, ground plastics, and fertilizers such as ammonium sulfate, ammonium phosphate, ammonium nitrate, ureas and vegetable products such as cereal flour, bark meal, wood meal and nutshell meal, cellulose powder or other solid carriers.

The formulations generally contain from 0.1 to 95% by weight, preferably 0.5 to 90% by weight, of one of the compounds I, II or III or the mixture of compounds I and II. The active ingredients are employed for this purpose in a purity of from 90% to 100%, preferably 95% to 100% (according to NMR or HPLC spectrum.

The compounds I, II or III or the mixtures or the corresponding formulations are used by treating the harmful fungi, or the plants, seeds, soil, areas, materials or rooms which are to be kept free of them with a fungicidally effective amount of the mixture or of the compounds I and II on separate application. The use can take place before or after attack by the harmful fungi.

Examples of the synergistic effect of the mixtures according to the invention against harmful fungi The fungicidal action of the compounds and of the mixtures was shown by the following tests:

The active ingredients were prepared separately or together as 20% strength emulsion in a mixture of 70% by weight of cyclohexanone, 20% by weight of Nekanil® LN (Lutensol® AP6, wetting agent with emulsifying and dispersing action based on ethoxylated alkylphenols) and 10% by weight of Emulphor® EL (Emulan® EL, emulsifier based on ethoxylated fatty alcohols) and diluted to the required concentration with water.

Evaluation took place by establishing the percentage areas with attack on the leaves. These percentages were converted into efficacies. The efficacies to be expected for the active ingredient mixtures were determined by the Colby formula [R. S. Colby, Weeds 15, 20–22 (1967)] and compared with the observed efficacies.

Colby formula:

$$E = x + y - x \cdot y / 100$$

E efficacy to be expected, expressed as % of untreated control on use of the mixture of active ingredients A and B in concentrations a and b x the efficacy expressed as % of the untreated control on use of active ingredient A in concentration a y the efficacy expressed as % of the untreated control on use of active ingredient B in concentration b An efficacy of 0 means that the attack on the treated plants corresponds to that on the untreated control plants; an efficacy of 100 means that the treated plants showed no attack.

A. Efficacy against Plasmopara viticola (vine peronospora)

Pot vines (variety: Müller Thurgau) were sprayed to run-off with the active ingredient preparation. After 8 days, the plants were sprayed with a suspension of zoospores of the fungus Plasmopara viticola and initially stored at 24° C. and 100% humidity for 48 h.

The test plants were then left in a glasshouse at 20°–30° C. for 5 days. Before the assessment, the plants were stored at high humidity for a further 16 h. The evaluation took place by inspection of the undersides of the leaves.

| Active indgredient | Application rate [ppm] | Efficacy [%] |
|---|---|---|
| –/–* | – | 0 |
| Ia | 31 | 48 |
| Ia | 16 | 22 |
| II | 31 | 0 |
| II | 16 | 0 |
| Mixture [application rate] | Efficacy [observed] | Efficacy [calculated] |
| Ia + II 31 + 31 | 80 | 48 |
| Ia + II 16 + 16 | 48 | 22 |

* 77% attack of untreated control

We claim:

1. A fungicidal mixture comprising a) an oxime ether carboxylic ester Ia or Ib

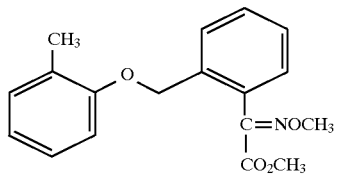

(Ia)

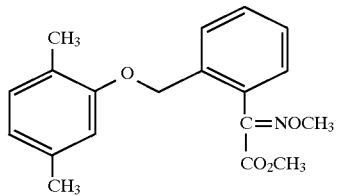

(Ib)

b) 1-(2-cyano-2-methoxyiminoacetyl)-3-ethylurea (II), and c) a dithiocarbamate III selected from the group consisting of manganese ethylenebis(dithiocarbamate) (zinc complex) (IIIa), manganese ethylenebis(dithiocarbamate) (IIIb), zinc ammoniate ethylenebis(dithiocarbamate) (IIIc) and zinc ethylenebis(dithiocarbamate) (IIId)

in a synergistically effective amount.

2. The fungicidal mixture as defined in claim 1, wherein the ratio by weight of compound Ia or Ib to the compound II is from 10:1 to 0.1:1.

3. The fungicidal mixture defined in claim 1, wherein the ratio by weight of compound Ia or Ib to the compound III is from 1:50 to 1:1.5.

4. A method for controlling harmful fungi, which comprises treating the harmful fungi, their habitat or the plants, seeds, soil, areas materials or rooms which are to be kept free of them with an effective amount of the mixture defined in claim 1.

5. The method of claim 4, wherein compound Ia or Ib and compound II are applied simultaneously together or separately or successively.

6. The method of claim 4 wherein the harmful fungi, their habitat or the plants, seeds, soil, areas, materials or rooms to be kept free of them are treated with from 0.01 to 0.5 kg/ha of the compound Ia or Ib.

7. The method of claim 4, wherein the harmful fungi, their habitat or the plants, seeds, soil, areas, materials or rooms to b kept free of them are treated with from 0.01 to 0.5 kg/ha of the compound II.

8. The method of claim 4, wherein the dithiocarbamate III is used in amounts of from 2:1 to 50:1 based on compound Ia or Ib.

* * * * *

UNITED STATES PATENT AND TRADEMARK OFFICE
CERTIFICATE OF CORRECTION

PATENT NO.: 5,891,908

DATED: April 6, 1999

INVENTOR(S): AMMERMANN et al.

It is certified that error appears in the above-identified patent and that said Letters Patent is hereby corrected as shown below:

Col. 6, claim 7, line 38, "b kept" should be --be kept--.

Signed and Sealed this

Seventeenth Day of August, 1999

Attest:

Attesting Officer

Q. TODD DICKINSON

Acting Commissioner of Patents and Trademarks